United States Patent [19]

Kelkar et al.

[11] Patent Number: 5,507,980
[45] Date of Patent: Apr. 16, 1996

[54] BASIC INORGANIC BINDERS

[75] Inventors: Chandrashekhar P. Kelkar, Plum Boro; Alain A. Schutz, Monroeville Boro; Leonard A. Cullo, Hempfield Township, Westmoreland County, all of Pa.

[73] Assignee: Aristech Chemical Corporation, Pittsburgh, Pa.

[21] Appl. No.: 380,866

[22] Filed: Jan. 30, 1995

Related U.S. Application Data

[63] Continuation-in-part of Ser. No. 85,804, Jul. 6, 1993, Pat. No. 5,399,329.
[51] Int. Cl.$^6$ ............................... C01C 1/26; B22D 11/01
[52] U.S. Cl. ..................... 264/15; 264/117; 264/211.11; 264/234; 423/420.2; 502/63; 502/251; 502/341; 502/414; 502/527
[58] Field of Search ............................... 264/234, 15, 117, 264/211.11; 423/420.2; 502/527, 341, 63, 251, 414

[56] References Cited

U.S. PATENT DOCUMENTS

| | | | |
|---|---|---|---|
| 3,796,792 | 3/1974 | Miyata et al. | 423/250 |
| 3,879,523 | 4/1975 | Miyata et al. | 423/250 |
| 3,879,525 | 4/1975 | Miyata et al. | 423/277 |
| 4,351,814 | 9/1982 | Miyata et al. | 423/306 |
| 4,458,026 | 7/1984 | Reichle | 502/80 |
| 4,656,156 | 4/1987 | Misra | 502/415 |
| 4,774,212 | 9/1988 | Drezdon | 502/62 |
| 4,970,191 | 11/1990 | Schutz | 502/341 |
| 4,977,123 | 12/1990 | Flytzani-Stephanopoulos et al. | 502/84 |
| 5,055,620 | 10/1991 | Schutz | 568/353 |
| 5,153,156 | 10/1992 | Schutz et al. | 502/63 |
| 5,182,242 | 1/1993 | Marler | 502/66 |
| 5,202,496 | 4/1993 | Schutz et al. | 568/388 |
| 5,253,991 | 10/1993 | Yokota et al. | 264/15 |
| 5,292,910 | 3/1994 | Raths et al. | 502/341 |
| 5,399,329 | 3/1995 | Schutz et al. | 423/415.1 |

OTHER PUBLICATIONS

F. Cavani et al, "Hydrotalcite-Type Anionic Clays: Preparation, Properties and Applications", Catalysis Today, vol. 11, No. 2, Dec. 2, 1991, pp. 173–301.
Vista Chemical Company, Technical Information, "Use of CATAPAL Alumina as a Bond", 1406B-RLA2091-7/ 87-1M, 6 pages. (No date available).
ASTM Publication, "Standard Test Method for Single Pellet Crush Strength of Formed Catalyst Shapes", Designation: D 4179-88a, Jan. 1989, pp. 622–624.

*Primary Examiner*—Wayne Langel
*Attorney, Agent, or Firm*—William L. Krayer

[57] ABSTRACT

The present invention relates to a process for making novel catalysts, catalyst supports, and adsorbers comprising synthetic hydrotalcite-like binders, having a sheet-like morphology and a sheet broadness to thickness ratio of at least 50 and a formula $Mg_{1-x}Al_x(OH)_2 \cdot xA^- \cdot mH_2O$ where $A^-$ is a mono carboxylic anion of the form $RCOO^-$ where R is $C_nH_{2n+1}$ and n=0–5, and x and m are numbers satisfying the following conditions:

$$0.2 \leq x \leq 0.4$$

$$0.0 \leq m \leq 4$$

This hydrotalcite-like material is combined with an inorganic material to form shapes which have good mechanical strength. The process includes starting with a synthesis mixture having magnesium (divalent cation) to aluminum (trivalent cation) molar ratio between 1:1 and 10:1, mono carboxylic anion to aluminum (trivalent cation) molar ratio between 0.1:1 to 1.2:1 and optionally added other anions. The process further includes reacting a mixture containing magnesium and aluminum cations and mono carboxylic anions in an aqueous slurry at a temperature of at least 40° C. and a pH of at least 7. The crystallized hydrotalcite product is then spray dried. This spray dried product is mixed with an inorganic material and water to form a plasticized mixture. The plasticized mixture is formed into various shapes. These shapes are then dried to remove water, calcined, steam treated, or otherwise tailored to the requirements of its specific application.

18 Claims, 6 Drawing Sheets

BASIC INORGANIC BINDERS

RELATED APPLICATION

This is a continuation-in-part of our application Ser. No. 085,804, filed Jul. 6, 1993, entitled "Hydrotalcite-like Materials Having a Sheet-like Morphology and Process for Production Thereof" U.S. Pat. No. 5,399,329.

TECHNICAL FIELD

This invention relates to binders made from hydrotalcite-like compounds. These hydrotalcite-like compounds have a unique sheet-like morphology, defined as broad and thin crystals having a breadth to thickness ratio of more than 50. The invention further relates to a process for the production of catalysts, catalyst supports, and adsorbers comprising these hydrotalcite-like binders. The hydrotalcite-like materials are mixed with inorganic materials, and water. The resulting mixture is formed into various shapes which are, after drying or calcining, mechanically strong.

BACKGROUND OF THE INVENTION

The present invention relates to a process of using a unique hydrotalcite material as a binder for different inorganic materials such as oxide, hydroxide, spinels, and zeolites to form extrudates, spheres, or tablets which are stable and possess good mechanical strength. These inorganic materials can then be used in their respective applications as catalysts, catalyst supports or adsorbers.

In many industrial applications involving fluid-solid contacting, the catalysts or adsorbers are loaded into a fixed bed reactor in preformed shapes. The formed shapes offer the advantages of lower pressure drop and efficient fluid distribution. In these applications it is beneficial to prevent the breakup and degradation of the formed shapes under the specific process conditions. Otherwise, the result will be an increase in the pressure drop and channeling which leads to inefficient contacting. Usually the forming of an active component to be used as a catalyst or adsorber is accomplished with the aid of a binder.

Choosing the binder to be used is important since the binder itself usually contributes to the reaction. The most commonly used binders are pseudoboehmite and cationic clays such as bentonite. These materials are fairly easy to extrude and provide extrudates having excellent physical strength. Pseudoboehmite, upon calcination, converts to a gamma alumina which is a well-known acidic support. Bentonite, and other such clays, are also known to catalyze reactions via the acidic pathway. In many cases it is crucial to suppress the undesirable side reactions catalyzed by the acidic nature of the support by adding alkaline components. The acidity generated by the binder can lead to cracking reactions in catalytic applications for hydrocarbon conversion. This can lead to coking of the catalyst, and decreased catalyst cycle length (see U.S. Pat. No. 5,182,242). In such cases, a binder with neutral or basic properties can inhibit undesirable side reactions.

Hydrotalcite is a naturally occurring mineral having the formula:

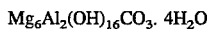

Hydrotalcite-like materials or anionic clay minerals have similar structures and have the general formula:

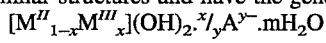

where $M^{II}$ and $M^{III}$ are divalent and trivalent cations, respectively, and A is an anion. These materials belong to the pyroaurite-sjogrenite class of minerals and their crystal structure has been described in the literature (Allmann, R., Acta Cryst. (1968), B24,972); Cavani et al., "Catalysis Today", 11, 173(1991) and references therein).

The most common approach to synthesis of hydrotalcites is by co-precipitation of the two cations under conditions of supersaturation (U.S. Pat. Nos. 4,165,339, 3,879,523 and references therein). They are also synthesized by reacting activated magnesia with an aqueous solution of sodium aluminate, carbonate, and hydroxyl ions (U.S. Pat. No. 4,904,457). It is well known that hydrotalcites prepared by the above procedures have a hexagonal plate-like crystal habit (Reichle, W. T., Chemtech, 1986, 58). When crystallized at room temperature, the crystallites have a diameter of approximately 0.01 to 0.1 microns and can be grown to about 1 to 5 microns by hydrothermal treatment. In all cases, the ratio of the diameter to thickness of the hexagonal crystals in such synthetic materials of the prior art is in the range of about 5 to 10. Scanning and transmission electron microscope (TEM) pictures of hydrotalcite with the hexagonal plate-like crystal morphology are shown in FIGS. 1a and 1b, respectively.

The reaction of a basic magnesium compound having a needle like structure with a suitable aluminum compound under basic conditions results in the synthesis of hydrotalcites with a needle like morphology (U.S. Pat. No. 4,351,814).

The term "hydrotalcite-like" is recognized in the art. It is defined and used in a manner consistent with usage, herein in the comprehensive literature survey of the above-referenced Cavani et al article.

For a catalyst to have good mechanical strength, the crush strength of a typical ¹⁄₁₆' extrudate would have to be at least in excess of 0.5 lb/mm, preferably in excess of 1 lb/mm and most preferably in excess of 2 lb/mm. The formed shapes prepared from the previously known synthetic hydrotalcites have strength of less than 0.1 lb/mm. U.S. Pat. No. 4,656,156 has mentioned that "Activated hydrotalcite is difficult to form in shapes, such as spheres, pellets and extrudates which are commonly used for adsorption and for catalyst substrates" (page 4, lines 7–10), and these hydrotalcites are clearly not suitable as-binders for other inorganic materials.

The object of the present invention is to provide novel hydrotalcite-like materials which will act as excellent binders for oxide, hydroxide and other inorganic materials used as catalysts, catalyst supports, and adsorbents. It is also the object of the invention to provide a method for synthesizing these hydrotalcites via a method which makes them suitable for use as binders. A further object of the invention is to describe a method for using these binders with different inorganic materials to form shapes with good mechanical strength.

SUMMARY OF THE INVENTION

We worked on synthesizing hydrotalcites using variations in the magnesium and aluminum compounds and more importantly, with mono carboxylic organic acids such as formic, acetic, propionic and isobutyric, having the following formula:

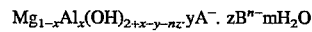

where $A^-$ is a mono carboxylic anion, B is OH or an optionally added anion or a combination of anions, x, y, z and m are numbers satisfying the following conditions:

0.2<x<=0.4

0.1<y<=0.5

0<z<=0.4

0<=m<=4.0

1<=n<=3

From the above it will be seen that, where B is not present, (where z=0), the basic formula of our materials is $Mg_{1-x}Al_x(OH)_2 \cdot xA^- \cdot mH_2O$. The mono carboxylic anion $A^-$ may be substituted by one or more different anions having an average valence of n, up to about 90 mole percent. We discovered that hydrotalcite-like materials with a sheet-like morphology (hereafter referred to as "sheet hydrotalcites") are generally crystallized when monocarboxylic anions are used, for balancing the positively charged hydroxide structure, in the synthesis. Electron microscope photographs of the new materials are shown in FIGS. 2a, 2b, 3 and 4. Interestingly dicarboxylic acids and other polycarboxylic acid compounds will not operate to make the sheet hydrotalcite-like materials of our invention.

It was found that these hydrotalcite materials can be easily produced by a commercially advantageous process. The new crystal morphology could also be formed when magnesium was partially (up to about 50 mole percent) substituted from a family of cations consisting essentially of Ni, Co, Zn, Cu, Mn; and aluminum was partially (up to about 50 mole percent) substituted from a family of cations consisting essentially of Cr and Fe.

It has also been found that the sheet hydrotalcite has several useful characteristics arising from the sheet crystal habit with crystal broadness to thickness ratio of greater than 50. In contrast to the previously known hydrotalcites, these sheet hydrotalcites can be mixed with any inorganic material and an appropriate amount of water to prepare a plasticized mixture which can be formed into shapes with good mechanical strength. These shapes retained their mechanical strength after calcination when exposed to the high temperatures used in most catalytic applications and also when subjected to steam.

It is the object of the present invention to provide a novel binder comprising sheet hydrotalcite material.

It is also the object of this invention to provide a process for producing novel catalysts, catalyst supports, and adsorbers comprising this binder.

DETAILED DESCRIPTION OF THE INVENTION

Figure 1A:
FIG. 1a is the scanning electron microscope picture of a conventional hexagonal hydrotalcite known in prior art taken at 20,000 X.
Figure 1B:
FIG. 1b is the transmission electron microscope picture of the same hydrotalcite taken at 50,000 X.
Figure 2A:
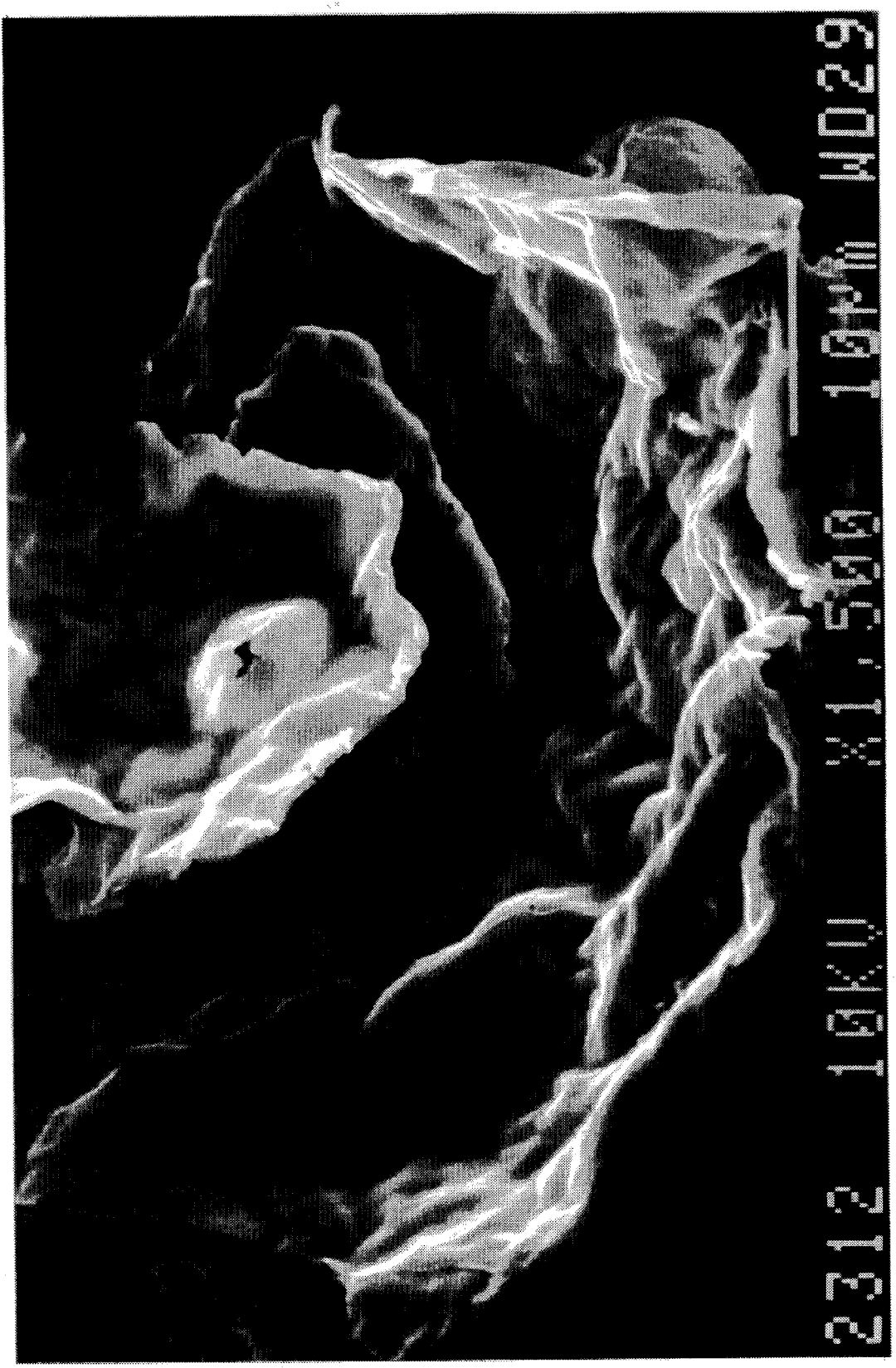
FIG. 2a is the scanning electron microscope picture of the sheet hydrotalcite produced according to this invention using acetic acid taken at 1500 X (Example 1).
Figure 2B:
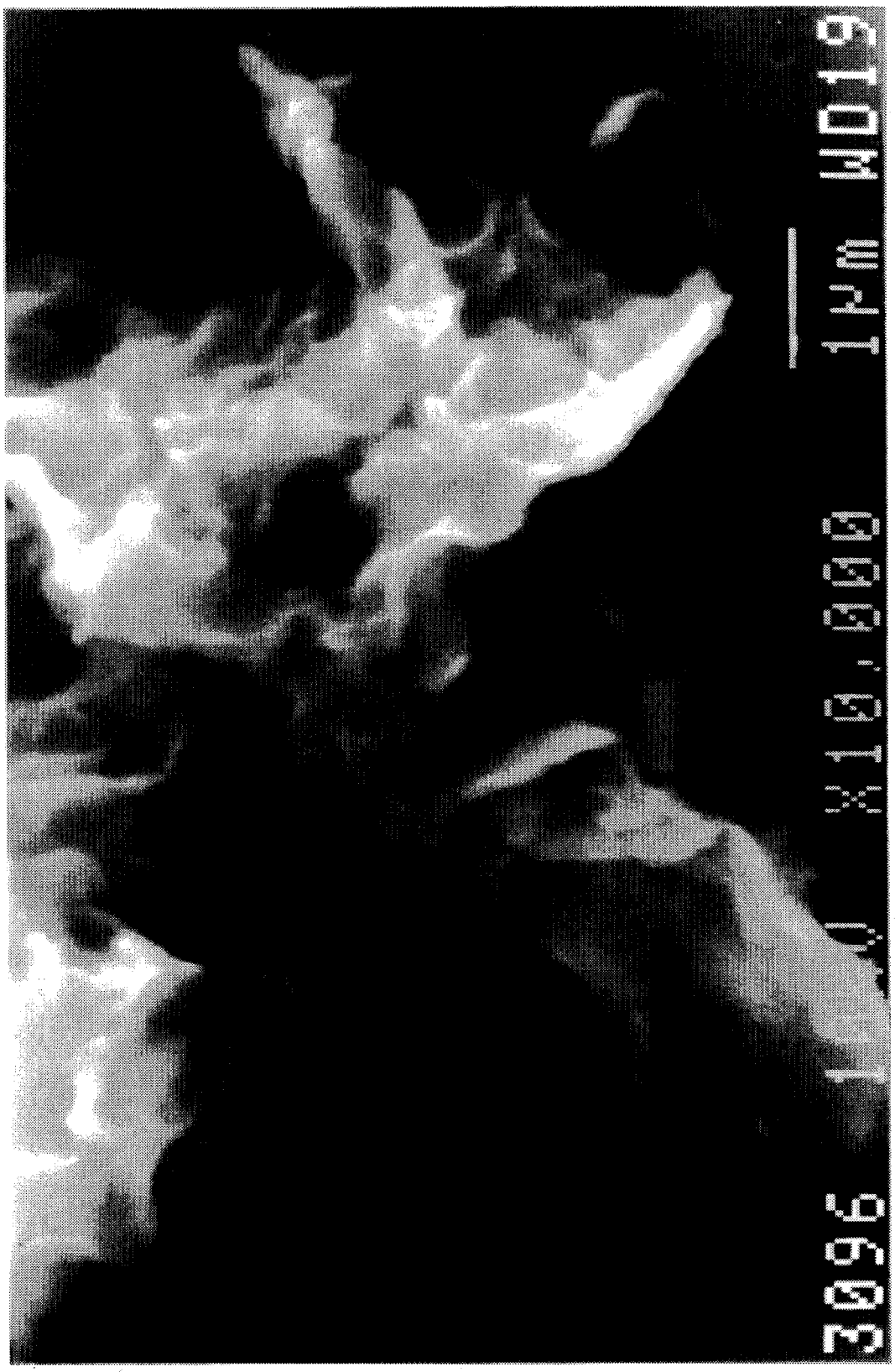
FIG. 2b is the scanning electron microscope picture of the sheet hydrotalcite produced according to this invention using isobutyric acid taken at 10,000 X.
Figure 3:
FIG. 3 is a transmission electron microscope picture of the sheet hydrotalcite produced according to this invention using acetic acid taken at 50,000 X (Example 1).
Figure 4:
FIG. 4 is a transmission electron microscope picture of the sheet hydrotalcite prepared by starting with a hexagonal hydrotalcite, calcining and recrystallizing in the presence of acetic acid taken at 10,000 X.

A comparison of FIGS. 1a with 2a and 2b shows that the hydrotalcite of this invention differs from the conventional hydrotalcite having a hexagonal plate-like structure. The hydrotalcite of the present invention also differs from the needle-like hydrotalcite described in U.S. Pat. No. 4,351, 814. As seen from FIG. 2a the longitudinal dimension of the sheet is much larger than the thickness. The ratio is so large that the sheets are pliable and are crumpled. The longitudinal dimensions of the sheets can be measured with relative accuracy from SEM pictures (FIGS. 2a, 2b). As seen from FIG. 2a, the ratio of the maximum longitudinal dimension to the minimum longitudinal dimension is less than 5. More often the ratio is very close to unity. In the discussion which follows, the breadth of the sheets will refer to the maximum longitudinal dimension. The breadth was calculated by averaging the maximum longitudinal dimension of at least ten different sheet crystallites. The sheet hydrotalcite of the present invention has sheets where the breadth ranges from about 5–500 microns.

The thickness of the sheets is estimated from the specific surface area and the density. The thickness of the sheets is calculated from the following equation:

$$\text{thickness} = \frac{2}{\text{surface area} \times \text{density}}$$

where the surface area is measured by BET method and the density of the hydrotalcite-like materials can be calculated for different cation pairs and anions by crystallographic means. The skeletal densities calculated for hydrotalcite-like material having the Mg, Al cation pair in a molar ratio of 2.0:1 of Mg/Al, dried overnite at 60° C. with different anions in the interlayer, are listed in the table below.

TABLE

| Skeletal Densities of Different Hydrotalcite-Like Materials (g/cc) | |
|---|---|
| Mg—Al-formic | 2.01 |
| Mg—Al-acetic | 1.77 |
| Mg—Al-propionic | 1.38 |
| Mg—Al-isobutyric | 1.32 |

Based on the above formula, the thickness of the sheet hydrotalcite-like material of the present invention is calculated to be about 0.005 to 0.1 microns. Therefore the ratio of breadth to thickness of the sheet hydrotalcite-like materials of the present invention is at least 50, generally up to about 5000, and more typically of the order of 500–1500.

The sheet hydrotalcites of the present invention are made by contacting an aluminum compound with a magnesium compound in water, together with a carboxylic acid having up to 6 carbon atoms. The aluminum source can be in the form of a reactive oxide, hydroxide, anionic salt or a mono carboxylic acid salt, the preferred source of aluminum is sodium aluminate or pseudoboehmite, with pseudoboehmite being the most preferred. Inorganic salts of the trivalent cation, e.g. aluminum nitrates, are not preferred for use as a source for the present invention. The magnesium source may be in the form of oxide, hydroxide or a mono carboxylic acid salt. Inorganic salts of the divalent cation, e.g. magnesium nitrate are not preferred for use as a source for the present invention. The magnesium source is added such that the molar ratio of divalent to trivalent metal is about 1:1 to 10:1; preferably between 2:1 and 3:1. The preferred source of Mg is either magnesium oxide or magnesium hydroxide, mono carboxylic salts of magnesium such as magnesium acetate or magnesium formate, the most preferred source being magnesium oxide. The amount of water soluble mono carboxylic acid equivalents is added such that the ratio of organic acid anion to trivalent cation is preferably 1:1 on a molar basis, but may vary from 0.1:1 to 0 1.2:1. In cases where the ratio is less than unity the rest of the charge is balanced by hydroxyl anions present in the synthesis medium. Optionally, an inorganic anion or a combination of inorganic anions is present in the synthesis mixture, and is incorporated into the layers instead of the hydroxyl ions. In any case it is preferred for the purposes of the present invention that at least 10 mole percent of the anions in the synthesis mixture be monocarboxylic anions. The mono carboxylic acid equivalents are added either in the form of the acid or as salts of any of the combination of cations being used. The final pH of the synthesis mixture should be between 7 and 12 but preferably between 8 and 9. Heating and mixing the above reaction mixture will facilitate the crystallization reaction. The reaction time can extend from 0.5 h to several hours, i.e. as much as 72 h or more depending on the reaction temperature and mixing. The crystallization is carried out at a temperature of at least 40° C. and atmospheric pressure. The rate of crystallization can be accelerated by increasing the temperature. The synthesis can also be carried out at higher than atmospheric pressures in a closed system, in which case the temperature can exceed 100° C. and the time of reaction is further shortened. The preferred crystallization temperature is about 60° to 100° C., but more preferably between 85° and 95° C. and atmospheric pressure. After the crystallization period, the product consists of a thick homogeneous slurry.

It was also discovered that the hydrotalcites of the present invention could also be synthesized starting from the hexagonal hydrotalcites. It is known in the literature that calcined hydrotalcite-like materials have the capacity to reconstitute the original layered structure upon exposure to water (U.S. Pat. No. 5,079,203). The temperature of calcination is critical and should not exceed 500° C. If the calcined hexagonal hydrotalcite-like material is recrystallized in a aqueous solution containing a monocarboxylic organic anion of the form RCOO–, where R is $C_nH_{2n+1}$ and n is an integer from 0 to 5, sheet hydrotalcite-like material is reconstituted. This route provides a method of transforming the hexagonal hydrotalcite made by other methods to the sheet hydrotalcite-like material of the present invention.

It is clear that the presence of a water soluble mono carboxylic anion is the key in the synthesis of sheet hydrotalcite.

A dried sample of the slurry shows an X-ray diffraction pattern characteristic to hydrotalcite materials but with expanded d-spacing due to the larger size of the intercalated organic anions. Typical X-ray diffraction lines of a crystalline sheethydrotalcite made with acetic acid have been identified and are shown in Table 1.

The crystallinity of the material can vary depending on the reaction temperature, time and mixing. Most of the sheet hydrotalcites, according to this invention, show diffraction patterns with strong OOl lines and weak and sometimes ill-defined hkO lines. Again this is the result of the unique morphology of the crystals. An easy characterization of crystallinity consists of depositing a few drops of synthesis suspension on a glass slide, drying and analyzing by X-ray diffraction. As commonly used with layered structures, this method orients the crystals and enhances the OOl lines. Several d(OO3) spacings, obtained with different mono carboxylate anions are shown in Table 2. Samples for scanning electron microscopy were prepared by freeze drying the slurry to prevent the rolling up of sheets as would normally occur in a regular drying process.

The hydrotalcite, after synthesis, may be washed (if necessary) and dried. The drying process can be carried out in an oven, but for the production of strong binder material it is preferable to spray dry the slurry. A typical solid particle made by spray drying has unexpected and unique properties which are characterized by dispersability and a swelling nature. The spray dried hydrotalcite, when mixed with water, forms a homogenous gel due to rehydration and dispersion into the original crystallites. In contrast, hydrotalcite like materials made by the above procedure, which are dried in an oven and then ground, are difficult to rehydrate or disperse. In the forming steps described below greater mechanical strength is achieved if the hydrotalcite added forms a homogenous gel. Therefore, for the purpose of the present invention it is preferred that the hydrotalcite like material be used as a spray dried powder.

The forming of different inorganic materials comprises one or more of the following steps: (1) The inorganic material(s) are mixed with the spray dried hydrotalcite and an effective amount of water to form a plasticized mixture. Applicants preferably use an inorganic material which is selected from the group consisting of single metal oxides, mixed metal oxides and physical mixture of metal oxides of metals chosen from groups IIA to IVA and the transition metal series. For the purposes of the present invention, the CAS version of the periodic table is used for nomenclature. It is well known in literature (Cavani et al., "Catalysis Today", 11, 173(1991)) that hydrotalcites lose 35% of their weight upon calcination to temperatures of 350° C. and above. Many catalytic applications necessitate pretreatment of the formed shapes at temperatures of 300° C. or above. Hence for the purposes of the present invention the weight percentage of hydrotalcite used as a binder will refer to the weight percentage on a calcined basis.

The weight percentage of the hydrotalcite used as a binder must be an effective amount, but will vary depending on the application for which the final inorganic composite is used. Increasing the weight percentage of the hydrotalcite in the mix will increase the mechanical strength of the final composite. The lower limit of the weight percentage of hydrotalcite used will be determined by the final application of the composite, but in all cases for the purposes of the present invention hydrotalcite is a necessary ingredient of the final composite which, when formed into shapes, possesses good mechanical strength. The upper limit of the hydrotalcite content of the dry mixture in applicants' invention is about 50% by weight.

Water is a necessary ingredient in helping the hydrotalcite form a homogenous gel due to rehydration and dispersion of the original crystallites. Rehydration and then the subsequent dehydration during the drying process is important for forming bonds between the hydrotalcite and the inorganic material resulting in good mechanical strength in the final composite. Water also facilitates homogenous mixing of the inorganic material(s) with hydrotalcite- In cases where the inorganic composite is subsequently formed, water helps in forming a plasticized mixture. The water content of the mixture will be governed by the degree of homogeneity, method of forming, etc., but in all cases for the purposes of the present invention, an effective amount of water is a necessary ingredient. The upper limit of water content of the plasticized mixture can be up to 50% by weight.

In sum, the ranges for each of the three basic ingredients will vary widely. There are numerous combinations, each depending on the type of inorganic material and the physical properties (such as crush strength) desired. For example, once a specific minimal crush strength is determined and a specific inorganic material is chosen, the amount of hydrotalcite and water can easily be determined through minimal experimentation. The only restriction applicants place on the amount of hydrotalcite and water is that a minimal effective amount (but not more than the maximum amounts mentioned above) be added so that a formed product will possess good mechnical strength (i.e. have a crush strength for a 1/16" extrudate of at least about 0.5 lb/mm).

The binder of the present invention is characterized by the absence of a need for an acid for peptization, as is required by aluminas. It is also a characteristic property of the binder of this invention that no other agent is required to provide a formable mass. (2) The plasticized mixture is formed into different shapes by tableting, extruding or spherodizing. The preferred forming method is extrusion since shapes of very small cross section can be prepared. The extrusion process involves the use of a screw or auger type extruder. A distinguishing feature of the present invention was the ability to extrude different inorganic materials without using high compression forces beyond the limits achievable by screw extruders. (3) The formed shapes are gradually dried to remove all water without creating thermal stresses which can weaken the formed shapes. (4) The dried formed shape can then optionally be subjected to calcination at higher temperature, steam treatment, impregnation with other catalytically active materials or any other such operation known in the art.

The examples described in this invention were typically formed into cylindrical shapes 1/16" in diameter and 1/4" long. The crush strength of the formed extrudates was determined by a single pellet crush strength tester and following a procedure similar to that described by the ASTM procedure D4179-88a. The strengths reported are the radial crush strengths. Typically, at least 15-20 extrudates were individually crushed and the average crush strength was reported on a lb/mm basis.

TABLE 1

Powder diffraction pattern of sheet hydrotalcite synthesized in Example 1 dried at room temperature. Spacings in Å

| d spacing (Å) | Relative Intensity | Miller Indices |
|---|---|---|
| 12.50 | 100 | 0, 0, 3 |
| 6.46 | 22 | 0, 0, 6 |
| 4.22 | 37 | 0, 0, 9 |
| 3.08 | 4 | 0, 0, 12 |
| 2.57 | 14 | 0, 1, 5 |
| 2.36 | 13 | 0, 1, 8 |
| 1.51 | 14 | 1, 1, 6 or 1, 1, 0 |

TABLE 2 d(003) spacings for several sheet hydrotalcites made with different organic acids and dried at 60° C. (Examples 1–4).

| Carboxylic Anion | d(003) Spacing Å | Example |
|---|---|---|
| Formic | 7.64 | 1 |
| Acetic | 12.3 | 2 |
| Propionic | 13.02 | 3 |
| Isobutyric | 15.15 | 4 |

EXAMPLE 1

This example describes a procedure for the synthesis of a typical sheet hydrotalcite to be used as a binder. 15.5 g of pseudoboehmite (versal 850) was slurried in 500 ml of deionized water. 13.7 g of acetic acid was added to the slurry. The suspension was vigorously agitated and heated to 50°–60° C. for 0.5 hr. Then 17.7 g magnesium oxide (Magchem 10-325 from Martin Marietta) along with 1.51 of deionized water were added to the resulting mixture and heated to 85°–95° C. for 6 hr. The ratio of magnesium to aluminum in the mixture is 2:1 and the ratio of carboxylic anion to aluminum was 1:1. A portion of the slurry was dried at 60° C. and X-ray diffraction carried out to confirm the hydrotalcite phase. TEM was performed on another portion of the slurry to confirm the presence of sheet hydrotalcite. Surface area of a sample dried and conditioned at 150° C. was about 35 m2/g, which corresponds to about 0.03 micron in thickness. The average breadth of the sheets was determined from SEM pictures to be 30 microns, yielding a ratio of breadth to thickness of 1000. The slurry was then spray dried to generate novel sheet hydrotalcite binder of the present invention.

EXAMPLE 2

326 g of Titanium dioxide was mixed with 135 g of hydrotalcite of Example 1 and dry mixed for 5 min., 120 g of water was then added to yield a paste of extrudable consistency. The paste was extruded through a 1" laboratory extruder into 1/16" diameter extrudates. The extrudates were dried overnight at 100° C. and calcined at temperatures of 400, 600, and 800 for 2 hr. The extrudates had a 20% weight of hydrotalcite as a binder on a calcined basis. The crush strength of the pellets after calcination is shown in Table I along with comparative samples for titanium dioxide.

TABLE I

Crush Strengths of Titanium Dioxide Catalysts

| | Calcination Temperature (C.) | Crush Strength (lb/mm) |
|---|---|---|
| Example 2 | uncalcined | 1.92 |
| | 400 | 1.02 |
| | 600 | 0.85 |
| | 800 | 0.74 |
| Comparative Ex. 2a | 400 | 0.43 |
| Comparative Ex. 2b | 400 | 0.19 |

Comparative Example 2a 258 g of Titanium dioxide was mixed with 113 g of hydrotalcite synthesized according to the procedure described in U.S. Pat. No. 3,879,525. Water was added to yield a paste of extrudable consistency. The paste was extruded through a 1" laboratory extruder into 1/16" extrudates. The extrudates were dried at 100° C. overnight and calcined at 400° C. for 2 hr. The crush strength is shown in Table I.

Comparative Example 2b 201 g of Titanium dioxide was mixed with water to yield a paste of extrudable consistency. The paste was extruded through 1" laboratory extruder into 1/16 extrudates. The extrudates were dried at 100° C. overnight and calcined at 400° C. for 2 hr. The crush strength is shown in Table I.

EXAMPLE 3

(a) 260 g of zinc oxide was mixed with 171 g of hydrotalcite and dry mixed. 109 g of water was added to yield a paste of extrudable consistency. The paste was extruded through a 1" laboratory extruder into 1/16" extrudates. The extrudates were dried overnight at 100° C. and calcined at 400° C. for 2 hr. The extrudates had a 30 weight percentage of hydrotalcite as a binder on a calcined basis. The crush strengths of the extrudates are shown in Table II. (b) 250 g of Zinc oxide was mixed with 97 g of hydrotalcite and extruded using the same procedure as Example 3(a). The extrudates had 20 weight percentage of hydrotalcite on a calcined basis. The crush strength after calcination is shown in Table II. (c) 274 g of zinc oxide was mixed with 22 g of hydrotalcite and extruded using the procedure in Example 3(a). The extrudates had a 5 weight percentage of hydrotalcite as a binder on a calcined basis. The crush strength after calcination is shown in Table II.

Comparative Example 3

308 g of Zinc oxide was mixed with water to yield a paste of extrudable consistency. The paste was extruded through a 1" laboratory extruder into 1/16" diameter extrudates. The extrudates were dried at 100° C. overnight and calcined to 400° C. for two hr. The crush strength is shown in Table II.

TABLE II

Crush Strengths of Zinc Oxide Catalysts

| | wt % hydrotalcite on a calcined basis | Crush Strength (lb/mm) |
| --- | --- | --- |
| Example 3(a) | 30 | 2.03 |
| Example 3(b) | 20 | 1.78 |
| Example 3(c) | 5 | 1.17 |
| Comparative Ex. 3 | 0 | 0.33 |

EXAMPLE 4

(a) 433 g of copper chromite (Engelhard Cu-1800P) was mixed with 170g of hydrotalcite. Water was added to yield a paste of extrudable consistency. The paste was extruded through a 1" laboratory extruder into 1/16" extrudates. The extrudates were dried overnight at 100° C. and calcined at 400° C. for 2 hr. The extrudates had a 20 weight percentage of hydrotalcite as a binder on a calcined basis. The crush strength of the extrudates is shown in Table III. (b) 156 g of copper chromite (Engelhard Cu-1800 p) was mixed with 118 g of hydrotalcite and extruded and calcined as described in Example 4(a). The extrudates had a 33 weight percentage as a binder on a calcined basis. The crush strength of the extrudates is shown in Table III. The crush strength of the extrudates were compared with commercially available extruded copper chromite catalyst (Cu-1230 E 1/16) from Engelhard which contains 33 percent by weight of binder.

TABLE III

Crush Strengths of Copper Chromite Catalysts

| | wt % HT on a calcined basis | Crush Strength (lb/mm) | Hg surface area (m2/g) | Pore Vol. (cc/g) |
| --- | --- | --- | --- | --- |
| Example 4(a) | 20 | 1.21 | 50 | 0.316 |
| Example 4(b) | 33 | 1.95 | 36 | 0.354 |
| Cu-1230 E 1/16 | — | 1.46 | 94 | 0.365 |

EXAMPLE 5

254 g of Sorbplus (Alcoa's proprietary mixed metal oxide hydroxide compound) was mixed 76 g hydrotalcite. Deionized water was added to make a paste of extrudable consistency. The resulting paste was extruded into 1/16" diameter extrudates, dried overnight at 100° C. and calcined at 400° C. for 2 hr. The crush strength of the extrudates is shown in Table IV.

Comparative Example 5

250 g of Sorbplus (Alcoa's proprietary mixed metal oxide hydroxide compound) was mixed with water to make a paste of extrudable consistency. The resulting paste was extruded into 1/16" diameter extrudates, dried overnight at 100° C. and calcined at 400° C. for 2 hr. The crush strength is shown in Table IV.

TABLE IV

Crush Strengths of Sorbplus

| | Calcination Temperature (C.) | Crush Strength (lb/mm) |
| --- | --- | --- |
| Example 5 | 400 | 1.10 |
| Comparative Ex. 5 | 400 | 0.36 |

EXAMPLE 6

255 g of Valfor 100, a commercial A zeolite obtained from PQ Corporation was mixed with 100 g of the sheet hydrotalcite for 5 minutes. 84 g of water was added to the mixer with vigorous mixing to obtain a paste of extrudable consistency. The resulting paste was extruded into 1/16" extrudates, dried overnight and calcined at 400° C. for 2 hr. The crush strength of the extrudates is 0.7 lb/mm.

EXAMPLE 7

2000 g of sheet hydrotalcite was added with 865 g of celite (Manville 545) and dry mixed. 560 g of water was added to form a paste of extrudable consistency. The paste was then extruded in a commercial extruder with a 1/20" trilobe die. The extrudates were dried overnight and calcined to 400° C. for 16 hr. Three portions of the calcined extrudates were exposed to in a fixed bed reactor at temperatures of 400, 500, and 600° C. respectively for 24 hr at a LHSV of 2 $h^{-1}$ The crush strengths of the steam treated extrudates were determined by a bulk crush strength test as follows: 20 g of the test sample was placed in a die 1.5" in diameter; the die was raised to appropriate pressure for 1 min with gentle tapping; the pressure was released and weight fraction less than 100 mesh sieve determined; the process was repeated with two different pressures and the results interpolated to determine the pressure required to generate 1 wt % fines. It is seen from Table V that these oxide(s) or hydroxide(s) bound with the sheet hydrotalcite maintain usable strength on exposure to steam at 600° C.

TABLE V

| Bulk Crush Strengths of Hydrotalcites After Steam Treatment | |
|---|---|
| Steam Treatment Temp. (C.) | Bulk Crush Strength (lb) |
| Untreated | 810 |
| 400 | 677 |
| 500 | 657 |
| 600 | 638 |

EXAMPLE 8

To demonstrate the effectiveness of the materials in the present invention, the material prepared in Example 4(b) was used to hydrogenate a stream containing 25% by weight of alpha methyl styrene(AMS) in cumene, to cumene in the liquid phase. The reaction was carried out in a jacketed ¼" tubular fixed bed reactor heated via an oil bath. 41 g of the extruded material of Example 4(b) was first reduced in pure hydrogen stream at 150° C. for 4 hr. The temperature was then lowered and a stream of AMS and cumene fed along with hydrogen. The conditions and test results are shown in the Table VI below. AMS is hydrogenated to cumene under these conditions with a greater than 99% selectivity. A similar comparative experiment was carried out using the commercial copper chromite extrudates (Cu-1230 E 1/16" available from Engelhard with identical results.

| Catalyst | Catalyst of Example 4(b) | Cu-1230 1/16" |
|---|---|---|
| Reaction Temp. (C.) | 110 | 109 |
| H2 flow (cc/min) | 187 | 183 |
| AMS(25%) + cumene flow (cc/hr) | 91 | 90 |
| Pressure (psig) | 140 | 140 |
| Conversion (wt %) | 97.3 | 96.7 |

We claim:

1. A process of making inorganic composite materials having good mechanical strength, comprising:
   contacting (i) an effective amount of a hydrotalcite-like material, in the form of a plurality of sheets, said sheets having an average broadness to thickness ratio of about 50:1 to 5000:1 and having the following composition:

$$(Mg_{1-x}Al_x)(OH)_2 \cdot xA^- \cdot mH_2O$$

wherein $A^-$ is a mono carboxylic anion of the form $RCOO^-$ where R is $C_nH_{2n+1}$ and n=0–5, x is a number between 0.2 and 0.4, and m is a number between 0 and 4, with (ii) at least one inorganic material and (iii) an effective amount of water, and then drying.

2. The process of claim 1 wherein the Mg in the hydrotalcite-like material is substituted up to about 50 mole percent by a divalent cation selected from the group consisting of Ni, Cu, Zn, Co, and Mn.

3. The process of claim 1 wherein the Al in the hydrotalcite-like material is substituted up to about 50 mole percent by a trivalent cation selected from the group consisting of Cr and Fe.

4. The process of claim 1 wherein the hydrotalcite-like material has a sheet broadness to thickness ratio of about 100:1 to 2000:1.

5. The process of claim 1 wherein the hydrotalcite-like material has a sheet broadness to thickness ratio of about 500:1 to 1500:1.

6. The process of claim 1 wherein the inorganic material is selected from the group consisting of single metal oxides, mixed metal oxides, and physical mixtures of oxides of metals from groups IIA to IVA and the transition metal series.

7. The process of claim 1 wherein the inorganic material is silica.

8. The process of claim 1 wherein the inorganic material is a spinel.

9. The process of claim 1 wherein the inorganic material is a zeolitic material.

10. The process of claim 1 wherein the amount of hydrotalcite-like material is up to about 50 weight percent of the contacted materials on a dry basis.

11. The process of claim 1 wherein the amount of water is up to about 50 weight percent of the contacted materials.

12. The process of claim 1 comprising the further step of forming the contacted materials into at least one shape before drying.

13. The process of claim 12 wherein the physical shape is formed by extrusion.

14. The process of claim 12 wherein the physical shape is formed by pelletizing said mixture.

15. The process of claim 12 wherein the physical shape is formed by spherodizing said mixture.

16. The process of claim 12 comprising the further step of calcining the physical shape.

17. The process of claim 12 comprising the further step of exposing the physical shape to steam at a temperature up to about 600° C.

18. The method of claim 13 wherein the extruded shape has a crush strength of at least about 1.0 lb/mm after drying.

* * * * *